US006866624B2

(12) United States Patent
Chornenky et al.

(10) Patent No.: US 6,866,624 B2
(45) Date of Patent: Mar. 15, 2005

(54) APPARATUS AND METHOD FOR TREATMENT OF MALIGNANT TUMORS

(75) Inventors: Victor I. Chornenky, Santa Rosa, CA (US); Vance Swanson, Santa Rosa, CA (US); Russell G. Hodge, Healdsburg, CA (US); Peter G. Davis, Windsor, CA (US)

(73) Assignee: Medtronic AVE,Inc., Santa Rosa, CA (US)

( * ) Notice: Subject to any disclaimer, the term of this patent is extended or adjusted under 35 U.S.C. 154(b) by 292 days.

(21) Appl. No.: 09/731,925

(22) Filed: Dec. 8, 2000

(65) Prior Publication Data

US 2002/0072645 A1 Jun. 13, 2002

(51) Int. Cl.[7] ................................................ A61N 5/00
(52) U.S. Cl. ...................... 600/3; 600/1; 600/2; 600/3; 600/4; 600/5; 600/6; 600/7; 600/8; 600/9; 600/10; 607/100; 607/101
(58) Field of Search ................. 600/1–10; 607/100–101

(56) References Cited

U.S. PATENT DOCUMENTS

| | | | |
|---|---|---|---|
| 2,531,583 A | | 11/1950 | Ott |
| 3,688,150 A | | 8/1972 | Wintzer |
| 4,448,198 A | | 5/1984 | Turner |
| 4,658,836 A | | 4/1987 | Turner |
| 4,662,383 A | | 5/1987 | Sogawa et al. |
| 4,676,258 A | | 6/1987 | Inokuchi et al. |
| 4,800,899 A | * | 1/1989 | Elliott ........................ 128/804 |
| 5,012,102 A | | 4/1991 | Gowlett |
| 5,057,106 A | * | 10/1991 | Kasevich et al. ............. 606/33 |
| 5,383,467 A | | 1/1995 | Auer et al. |
| 5,431,168 A | * | 7/1995 | Webster, Jr. ................ 128/658 |
| 5,582,171 A | | 12/1996 | Chornenky et al. |
| 5,737,384 A | * | 4/1998 | Fenn ............................. 378/65 |
| 5,854,822 A | | 12/1998 | Chornenky et al. |
| 5,944,749 A | | 8/1999 | Fenn |
| 6,022,308 A | * | 2/2000 | Williams ........................ 600/2 |

(List continued on next page.)

FOREIGN PATENT DOCUMENTS

EP       1 057 500 A1    12/2000

OTHER PUBLICATIONS

James R. Oleson; "Hyperthermia" in Cancer: Principles and Practice of Oncology, 2725–33 (DeVita et al. eds., 4th Edition 1993).
U.S. Appl. No. 08/701,764, filed Aug. 1996, Chornenky et al.
Ward, Roger W., "The Constants of Alpha Quartz." 14th Piezoelectric Devices Conference and Exhibition, Sep. 15–17, 1992, Sponsored by Components Group EIA, 1992, (See especially Table I, pp. 3–4).
U.S. Appl. No. 08/806,244, filed Feb. 1997, Chornenky et al.
U.S. Appl. No. 09/756,287, filed Jan. 2001, Chornenky et al.

*Primary Examiner*—Henry Bennett
*Assistant Examiner*—Nihir Patel
(74) *Attorney, Agent, or Firm*—Sterne, Kessler, Goldstein & Fox P.L.L.C.

(57) ABSTRACT

The present invention relates to a device for simultaneously treating a tumor or cancerous growth with both hyperthermia and X-ray radiation using brachytherapy. The device includes a needle-like introducer serving as a microwave antenna. Microwaves are emitted from the introducer to increase the temperature of cancerous body tissue. The introducer is an inner conductor of a coaxial cable. The introducer contains a hollow core which houses an X-ray emitter. The X-ray emitter is connected to a high voltage miniature cable which extends from the X-ray emitter to a high voltage power source. The X-ray emitter emits ionizing radiation to irradiate cancerous tissue. A cooling system is included to control the temperature of the introducer. Temperature sensors placed around the periphery of the tumor monitor the temperature of the treated tissue.

22 Claims, 4 Drawing Sheets

U.S. PATENT DOCUMENTS

| | | | | |
|---|---|---|---|---|
| 6,067,475 A | * | 5/2000 | Graves et al. | 607/101 |
| 6,069,938 A | | 5/2000 | Chornenky et al. | |
| 6,083,148 A | * | 7/2000 | Williams | 600/2 |
| 6,095,966 A | * | 8/2000 | Chornenky et al. | 600/3 |
| 6,108,402 A | | 8/2000 | Chornenky | |
| 6,113,593 A | * | 9/2000 | Tu et al. | 606/34 |
| 6,134,300 A | | 10/2000 | Trebes et al. | |
| 6,148,061 A | | 11/2000 | Shefer et al. | |
| 6,275,566 B1 | | 8/2001 | Smith et al. | |
| 6,319,188 B1 | * | 11/2001 | Lovoi | 600/3 |
| 6,319,189 B1 | * | 11/2001 | Halpern et al. | 600/3 |
| 6,464,625 B2 | * | 10/2002 | Ganz | 600/3 |
| 6,475,168 B1 | * | 11/2002 | Pugsley, Jr. et al. | 600/585 |

\* cited by examiner

APPARATUS AND METHOD FOR TREATMENT OF MALIGNANT TUMORS

BACKGROUND OF THE INVENTION

1. Field of the Invention

The present invention relates generally to an apparatus for treating and destroying harmful cells within the body. More particularly, the present invention relates to an apparatus for delivering heat and radiation to a tumor within a body to destroy the cells in the tumor.

2. Background Art

Hyperthermia, the heating of body cells to above 41° C. for therapeutic purposes, particularly to destroy cancer tumors, has been known and used in the past. It is also known that above 46° C., irreversible destruction of healthy and diseased body cells occurs. The purpose of hyperthermia equipment generally is to deliver heat preferentially to diseased body cells while maintaining adjacent healthy cells at acceptable temperatures, i.e., below the temperature at which irreversible cell destruction occurs.

There are three main theories which explain why hyperthermia is successful in fighting cancerous growths. Some scientists believe that heat produces a localized fever which causes lymphocytes to congregate (200 lymphocytes are usually needed to destroy one cancerous cell). Other scientists think heat improves the flow of blood in the tumor, and this increased blood flow, in turn, brings more oxygen to the tumor and lowers its Ph, thus starving the tumor cells by reducing nutrients. A third theory contends that the DNA forces that hold tumorous cells together are weaker than those of healthy cells and the heat applied to the tumorous cells breaks them apart and thereby destroys them more easily.

Hyperthermia or induced high body temperature is beneficial in treating many types of cancer. Some malignant cell masses having poorer heat dissipation characteristics than normal tissue, presumably due to abnormally low blood circulation, are subject to preferential hyperthermia treatment. As a result, such malignant cell masses can often be heated to temperatures substantially higher than that of surrounding healthy cells, to enable hyperthermia treatment, even when both types of cells are heated simultaneously. This characteristic not only enables hyperthermia treatment of some types of malignancies which are no more temperature sensitive than normal cells, but usually permits much shorter hyperthermia treatment times, even of thermally sensitive malignancies, as is important for various medical reasons.

More specifically, various types of malignant growths are considered by many researchers to have a relatively narrow hyperthermia treatment temperature range. Below a threshold temperature of about 41.5° C. (106.7° F.), thermal destruction of these malignancies is not believed to occur. In fact, for hyperthermia temperatures below this threshold, growth of some of these malignancies may tend to be stimulated. In contrast, at temperatures above a range of about 43° C. to 45° C. (109.4° F. to 113° F.) thermal damage even to most normal cells occurs, the exposure duration at any elevated temperature also being a significant factor. Accordingly, if large or critical parts of a human body are heated into, or above, the 43° C. to 45° C. range for even relatively short durations, serious permanent injury or death is possible.

Radiation treatment of malignant cells is also known. Radiation treatment is classified into two general categories. Teletherapy is treatment of cells within a body from an area external to the body. Radiation generated outside the body travels through the body to reach the malignant cells when the malignant cells are on the interior of the body. Thus, healthy cells are exposed to harmful, cell killing radiation. One way to minimize exposure of a cell at a specific point is to focus radiation over an area at the source to a point distant from the source, where the cells to be treated are at the focal point. In this way, only the malignant cells are exposed to the full power of the radiation. However, healthy tissue surrounding the malignant cells, and all cells between the malignant cells and the radiation producing device are still exposed to a large amount of radiation.

Brachytherapy, a second type of radiation treatment, is treatment of cells from a point or source on the interior of the body. Thus, brachytherapy has the advantage of allowing localized radiation treatment. A physician can treat malignant cells by radiating in an area in close proximity to, or within, a group of malignant cells such as a tumor, with only minimal exposure to radiation of healthy cells.

Recently, it was discovered that hyperthermia and radiation, used in combination, is more effective at killing malignant cells than either hyperthermia or radiation alone. Hyperthermia suppresses the repair mechanism of the cellular DNA which is damaged by ionizing radiation. At normal body temperatures, the time required for a cell to complete repair is about 30–45 minutes. At elevated temperatures, in the range of 42–45° C., the repair mechanism is disabled. Thus, while at elevated temperatures, the cell cannot repair the damage to the tumor caused by the radiation exposure. Therefore, the amount of radiation necessary to break down the tumorous cell is greatly reduced.

Currently, hyperthermia is used with radiation to treat malignant cells by using the combination of localized hyperthermia treatment to heat the cells, and teletherapeutic treatment to radiate the cells. Despite the advantages of treating malignant cells with both heating and radiation, there is not a brachytherapeutic apparatus capable of delivering both X-ray radiation and interventional heating to a malignant tumor. Therefore, what is needed is an apparatus that is capable of providing brachytherapeutic X-ray radiation and interventional heating to a malignant tumor.

BRIEF SUMMARY OF THE INVENTION

The present invention relates to a device for simultaneously treating a tumor or cancerous growth with both hyperthermia and X-ray radiation using brachytherapy. The device is comprised of a needle-like introducer serving as a microwave antenna. Microwaves are emitted from the introducer to increase the temperature of cancerous body tissue. As the temperature of the cancerous tissue increases, the tissue's resistance to radiation is lowered or eliminated. The introducer is an inner conductor of a coaxial cable. The coaxial cable allows the introducer to serve as a microwave emitter when an electrical current is passed through the metal braid portion of the coaxial cable and across a dielectric material. The coaxial cable extends to a microwave generator, which continuously generates microwaves at an adjustable frequency.

The introducer contains a hollow core which houses an X-ray emitter, which is connected to a high voltage miniature cable extending from the X-ray emitter to a high voltage power source. The X-ray emitter emits ionizing radiation to irradiate cancerous tissue. The X-ray emitter can be moved within the introducer to ensure that a sufficient radiation dose is provided to all of the target tissue. In particular, a mechanism advances and retracts the X-ray emitter within the introducer. Because a large proportion of the delivered power is converted to and emitted as heat by the X-ray emitter, a cooling system is included to control the temperature of the introducer. Flowing liquid coolant serves as a cooling mechanism for the X-ray emitter and the introducer.

Temperature sensors placed around the periphery of a tumor, monitor the temperature of treated tissue. As temperature begins to exceed a therapeutic temperature range, the temperature reading unit actuates a switch and the microwave generator is turned off or slowed down. If the temperature is below the therapeutic range, the temperature reading unit actuates a switch to activate the microwave generator to either turn on the unit or increase its power. In this way, the heat energy necessary to kill cancer cells in a growth does not exceed a level which might possibly harm healthy cells in the region surrounding the tumor.

In a second embodiment of a device for simultaneously treating a tumor or cancerous growth with hyperthermia and X-ray radiation, an introducer is comprised of a rigid plastic material, transparent to microwave radiation. The introducer includes a sharp tip for piercing skin and for entering a tumor. The device is designed to allow alternative doses of microwave radiation and X-ray radiation. The introducer is connected to an X-ray leg and a microwave leg. An X-ray emitter is located within a hollow core of introducer, and has a high voltage miniature cable extending through the X-ray leg. The X-ray emitter is attached to the high voltage miniature cable, which is connected to a push-pull device. The push-pull device can retract the X-ray emitter to a point outside of the introducer and into the X-ray leg.

A microwave antenna is connected to the distal end of a coaxial cable, which extends through the microwave leg, and a push-pull device. The microwave antenna can be advanced into the hollow core of the introducer, and retracted from the hollow core of the introducer into the microwave leg using the push-pull device.

In use, a controller operates to activate a high voltage source when the X-ray emitter is properly positioned within the introducer. The controller also controls the movement of the X-ray emitter by means of the push-pull device. The controller deactivates the high voltage source and activates the push-pull device to retract the X-ray emitter to an idle position in X-ray leg. The controller then activates the push-pull device to advance the microwave antenna from the microwave leg into the introducer. Once the microwave antenna is properly positioned, the controller activates the microwave generator to provide hyperthermia treatment to cancerous cells.

BRIEF DESCRIPTION OF THE DRAWINGS/ FIGURES

The foregoing and other features and advantages of the invention will be apparent from the following, more particular description of preferred embodiments of the invention, as illustrated in the accompanying drawings.

DETAILED DESCRIPTION OF THE INVENTION

A preferred embodiment of the present invention is now described with reference to the figures where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant art will recognize that other configurations and arrangements can be used without departing from the spirit and scope of the invention.

Biological tissue exhibits high absorption of low energy X-rays, such as X-rays in the 10–50 keV range. High absorption rates result in high gradients of radiation dose in tissue at or near an X-ray emitter, with only limited penetration of radiation into tissue beyond the immediate area of the X-ray emitter. Thus, local X-ray emission in a tumor can be very high, such as 100 Gy (the gray is the SI unit of measurement for absorbed dose of radiation; symbol=Gy), while still causing little damage to healthy cells surrounding the cancerous cells. Such a dose is high enough to kill even the most resistant to radiation (hypoxic) cells with radiation alone, without supplemental heating. As the distance from the X-ray source increases, the dose decreases to 30–45 Gy at the interface of the tumor and the healthy tissue. As the dose is reduced toward the edges of the tumor, it is helpful to increase temperature of the edge to more effectively destroy these cancerous cells. The present invention increases cell killing at the margin of tumors by preferential heating of this area.

Figure 1:
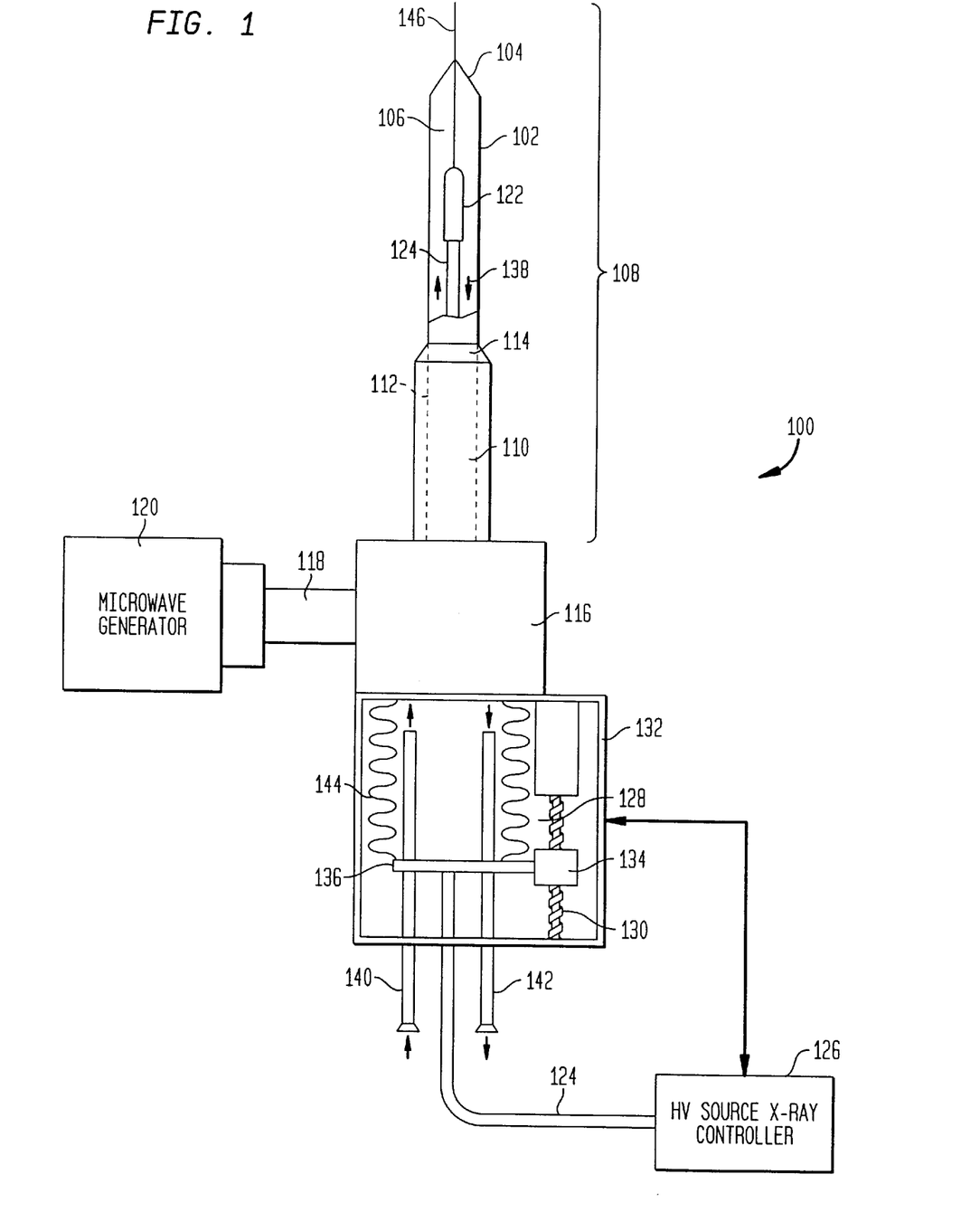
FIG. 1 is a schematic of a first embodiment of a device for simultaneously treating a tumor or cancerous growth with hyperthermia and X-ray radiation.

FIG. 1 shows a schematic of a first embodiment of a device 100 for simultaneously treating a tumor or cancerous growth with hyperthermia and X-ray radiation. Device 100 includes an introducer 102 having a distal tip 104. Distal tip 104 may be needle-like, having a sharp point to pierce and penetrate skin, tissue and cancerous clusters, such as tumors. For the most effective treatment, introducer 102 should be implanted approximately across the center of the tumor to be treated. However, some medical situations, such as advanced colon cancer, may have a plurality of cancerous conglomerates. In this case, introducer 102 is placed in the proximity of the tumors, such that many cancerous conglomerates can be simultaneously treated.

Introducer 102 is the exposed portion of an inner wire 112 of a coaxial cable 108. Coaxial cable 108 also includes a metal braid portion 110 serving as an outer conductor. Between inner wire 112 and metal braid portion 110 is an insulating dielectric material 114. The configuration of coaxial cable 108 allows introducer 102 to serve as a microwave emitter when an electrical current is passed through metal braid portion 110 and across dielectric material 114.

Coaxial cable 108 is connected to a connector 116 which serves as a coupling between coaxial cable 108 and a second coaxial cable 118, which extends from connector 116 to a microwave generator 120. Microwave generator 120 continuously generates microwaves at an adjustable frequency, such as 1.5 GHz.

The frequency of the microwaves generated from microwave generator 120 is usually in the range of 1–5 GHz. The frequency of the microwaves may be selected from a plurality of oscillation frequencies that can be generated from microwave generator 120 depending on the length of introducer 102, also serving as the microwave emitter. An optimal operating frequency can be selected to achieve penetration of the microwave radiation into the surrounding tissue, adequate for heating a particular sized tumor.

Microwave generator 120 can be of any desired construction. Preferably it is a commercially available product, such as one made by Matsushita Electric Industries, Ltd. of Tokyo, Japan. A generator can be modified so as to produce lower power output levels sufficient for the purposes to which the present invention is to be placed. Typically a microwave generator generates 15–100 watts of power, which is emitted through introducer 102 into surrounding tissue, warming the tissue.

Introducer 102 contains a hollow core 106 which houses an X-ray emitter 122. In FIG. 1, introducer 102 is shown with a cutout, revealing X-ray emitter 122. X-ray emitter 122 is connected to a high voltage miniature cable 124 which extends from X-ray emitter 122 to a high voltage power source 126. High voltage power source 126 delivers 25–50 kV through high voltage miniature cable 124 to X-ray emitter 122. High voltage miniature cable 124 is a miniature coaxial cable, having a center conductor connected to an anode and an outer conductor connected through an outer surface of emitter 122 to an anode, as described in detail with reference to FIG. 4.

X-ray emitter 122 emits ionizing radiation in a donut-like irradiation pattern, primarily in radial directions. Thus, as emitter 122 radiates cancerous tissue, it is necessary to move X-ray emitter 122 along a longitudinal axis 146 of introducer 102 so that a radiation dose is provided to all of the target tissue. A push-pull mechanism 128 advances and retracts X-ray emitter 122 within introducer 102. Push-pull mechanism 128 may be attached to connector 116 or may be located elsewhere, provided it is attached to high voltage miniature cable 124. Push-pull mechanism 128 advances X-ray emitter 122 toward distal tip 104 within introducer 102 by applying a compressive force, or pushing, high voltage miniature cable 124 from a point on high voltage miniature cable 124 located outside of the patient's body. Likewise, push-pull mechanism may retract X-ray emitter 122 away from distal tip 104 within introducer 102 by applying a tensile force, or pulling, high voltage miniature cable 124 from a point on high voltage miniature cable 124 located outside of the patient's body. Because X-ray emitter 122 is fixedly attached to high voltage miniature cable 124, any force applied to advance or retract high voltage miniature cable 124 will likewise advance or retract X-ray emitter 122.

Push-pull mechanism 128 may be any commonly available apparatus capable of displacing attached components, as would be apparent to one skilled in the relevant art. The embodiment shown in FIG. 1 shows a push-pull mechanism 128 comprising a threaded axle shaft 130 secured within a housing 132. Threaded axle shaft 130 is rotatable about its axis. A threaded nut 134, having the same thread gauge as threaded axle shaft 130, is threaded onto threaded axle shaft 130. Threaded nut 134 is secured in housing 132 such that threaded nut 134 does not rotate around threaded axle shaft 130. Thus, as threaded axle shaft 130 rotates, threaded nut 134 is moved linearly along threaded axle shaft 130.

A rigid bar 136 is fixedly secured to both threaded nut 134 and high voltage miniature cable 124. As threaded axle shaft is rotated about its axis, threaded nut 134, bar 136 and high voltage miniature cable 124 linearly move to advance or retract X-ray emitter 122. Push-pull mechanism 128 is preferably adapted to provide an automated, computer-controlled, continuous or step-wise motion. Operation of push-pull mechanism could be controlled by a remote control box. Preferably, push-pull mechanism is operated by a control box that includes both high voltage source 126 and control of push-pull mechanism 128, so that control of X-ray emitter 122 is completely controlled by-a single operating device. However, as would be apparent to one skilled in the relevant art, control of high voltage source 126 and push-pull mechanism 128 could be performed separately.

Due to inefficiencies common in X-ray devices, only a small fraction of the power delivered to X-ray emitter 122 by high voltage source 126 is converted to ionizing radiation. A large proportion of the delivered power is converted to and emitted as heat by X-ray emitter 122. Additionally, introducer 102 can generate heat as it is used as a microwave emitter. As stated above, it is desirable to control the heat output of device 100 so that healthy cells are not damaged. Furthermore, the searing of any cell within a body can be quite painful.

Device 100 includes a cooling system to control the temperature of introducer 102. Liquid coolant, denoted by arrows 138, serves as a cooling mechanism for X-ray emitter 122 and introducer 102. The cooling system is comprised of an inlet tube 140 and an outlet tube 142. Inlet tube 140 and outlet tube are each fluidly connected to hollow core 106. A liquid pump (not shown) is connected to inlet tube 140 and forces liquid through inlet tube 140 and into hollow core 106, thereby causing the liquid to be circulated through hollow core 106. Likewise, the pressure buildup inside hollow core 106 causes the liquid to exit through outlet tube 142. In a preferred embodiment, fluid exits outlet tube 142 into a reservoir (not shown), from which the pump draws liquid. In this way, the cooling fluid can be recycled. Alternatively, the fluid from outlet tube 142 could be discarded.

In this embodiment, inlet tube 140 and outlet tube 142 extend through housing 132 of push-pull device 128. Inlet tube 140 and outlet tube 142 are fixedly connected to rigid bar 136 and extend into a baffle 144. The interior of baffle 144 is fluidly connected to hollow core 106, allowing liquid to flow to X-ray emitter 122 and introducer 102. Baffle 144 is flexible to accommodate the linear movement of bar 136, while ensuring that no liquid leaks from hollow core 106. Although the sealing device in this embodiment is a baffle, it would be apparent to one skilled in the relevant art that the sealing of hollow core 106 could be done through o-ring seals, silicone or any other seal. Likewise, inlet tube 140 and outlet tube 142 need not necessarily extend through push-pull device 128, but may be connected through a separate device connected to connector 116 or through another location as would be apparent to one skilled in the relevant art. Additionally, inlet tube 140 and outlet tube 142 may be any configuration of tubes or holes in device 100 through which coolant can flow into hollow core 106. In one embodiment, inlet tube 140 and outlet tube 142 are concentric tubes extending into hollow core 106. Finally, inlet tube 140 and outlet tube 142 can extend deep into coaxial cable 108 and need not terminate prior to entering connector 116, as shown in FIG. 1.

Human tissue, including cancerous tissue, is comprised of about 80% water. It is important to roughly match the impedance of the tissue with the impedance of liquid coolant 138. Without impedance matching, a mismatch occurs, causing a significant reflection of emitted waves in the opposite direction of propagation. This is detrimental to the application as the reflected power will be additive to the forward moving power and as a result, over-heating will occur in the cable and in the patient's tissue. Over-heating can become significant enough to cause pain in the patient. Therefore, liquid coolant 138 preferably completely fills the volume of hollow core 106 to eliminate any voids or air pockets affecting the impedance of the system.

Liquid coolant 138 is preferably a fluid, such as distilled water, denatured alcohol or an optimized molal solution of water and salt in the temperature range of about 4–20° C. Such a temperature range cools not only X-ray emitter 122 and introducer 102, but cools surrounding tissue as well. By selecting the appropriate fluid, impedance matching is achieved and reflected power reduced to a few percent. Thus, overheating is eliminated and patient comfort is assured.

Figure 2:
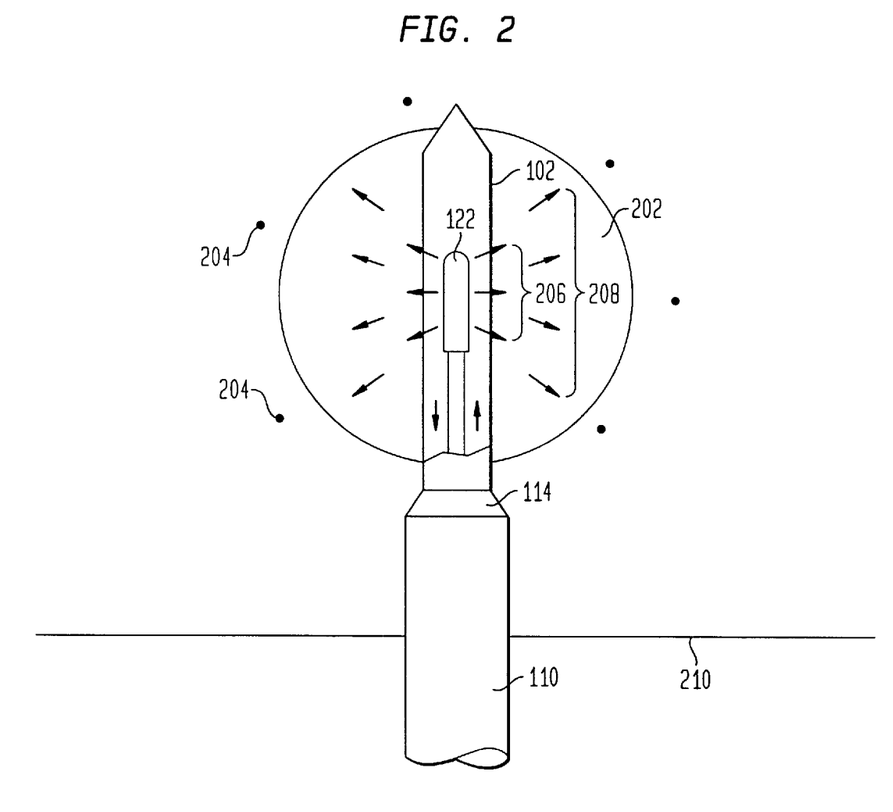
FIG. 2 shows the device of FIG. 1 in use for treating a tumor.

FIG. 2 shows introducer 102 and coaxial cable 108 in use. Introducer and coaxial cable 108 pierce and penetrate skin 210 and introducer 102 is inserted into a tumor 202. Biological tissue, such as tumor 202 exhibits strong absorption of low energy X-rays, such as X-rays in the 10–50 keV range. As X-ray radiation 206 travels through introducer 102 into the surrounding tissue, high gradients of radiation dose occur in the tissue at or near the emitter, within only limited penetration of radiation into the tissue beyond the immediate area of the emitter. Thus, local X-ray emission in a tumor can be very high, while still causing little damage to healthy cells surrounding the cancerous cells. Thus, the X-ray dose delivered in tumor 202 may be very high, such as 100 Gy. Such a dose is high enough to kill even the most resistant to radiation (hypoxic) cells with radiation alone, without supplemental heating. As the distance from the source increases, the dose decreases to 30–45 Gy at the interface of the tumor and the healthy tissue. Thus, as dose is reduced toward the edges of the tumor, it is helpful to increase temperature of the edge to more effectively destroy these cancerous cells.

As described above, introducer 102 serves as a microwave antenna, emitting microwave radiation 208 and heating the tumor and surrounding tissue for hyperthermia treatment. The hyperthermia treatment range is relatively narrow, having a threshold temperature of about 41.5° C. (106.7° F.). Below this threshold temperature, very little or no thermal destruction of malignancies is believed to occur, and in fact, for hyperthermia temperatures below this threshold level, growth of some malignancies may tend to be stimulated. In contrast, temperatures above a range of about 43° C. to 45° C. (109.4° F. to 113° F.) may cause thermal damage to most normal cells, considering also the factor of exposure duration. Therefore, it is critical to ensure that such overheating of healthy cells does not occur when treating with hyperthermia.

To monitor the temperature increase of surrounding cell structure due to microwave emission from introducer 102, temperature sensors 204 are placed around the periphery of tumor 202. Sensors 204 are coupled to leads (not shown) which, in turn, are coupled to a temperature reading unit (not shown). When signals from sensors 204 are directed to the temperature reading unit, the signals are used to indicate relative temperature values at the outer periphery of the tumor. In one embodiment, the temperature reading unit is electrically connected to a control unit switch (not shown) that controls an on-off or variable power switch of microwave generator 120 of FIG. 1. As temperature begins to exceed the therapeutic range of 43–45° C., the temperature reading unit actuates a switch and microwave generator is turned off or slowed down. If the temperature is below the therapeutic range, the temperature reading unit actuates a switch to activate the microwave generator which is turned on or increased in power. In this way, the heat energy necessary to kill cancer cells in a growth does not exceed a level which might possibly harm healthy cells in the region surrounding the tumor. Yet, once power is again applied to introducer 102, the introducer can radiate the energy so as to continue to heat the tumor to lower its resistance to the radiation emitted from X-ray emitter 122 for a time deemed necessary to kill the cancerous growth therein. Overall, the procedure averages about 30–60 minutes.

Figure 3:
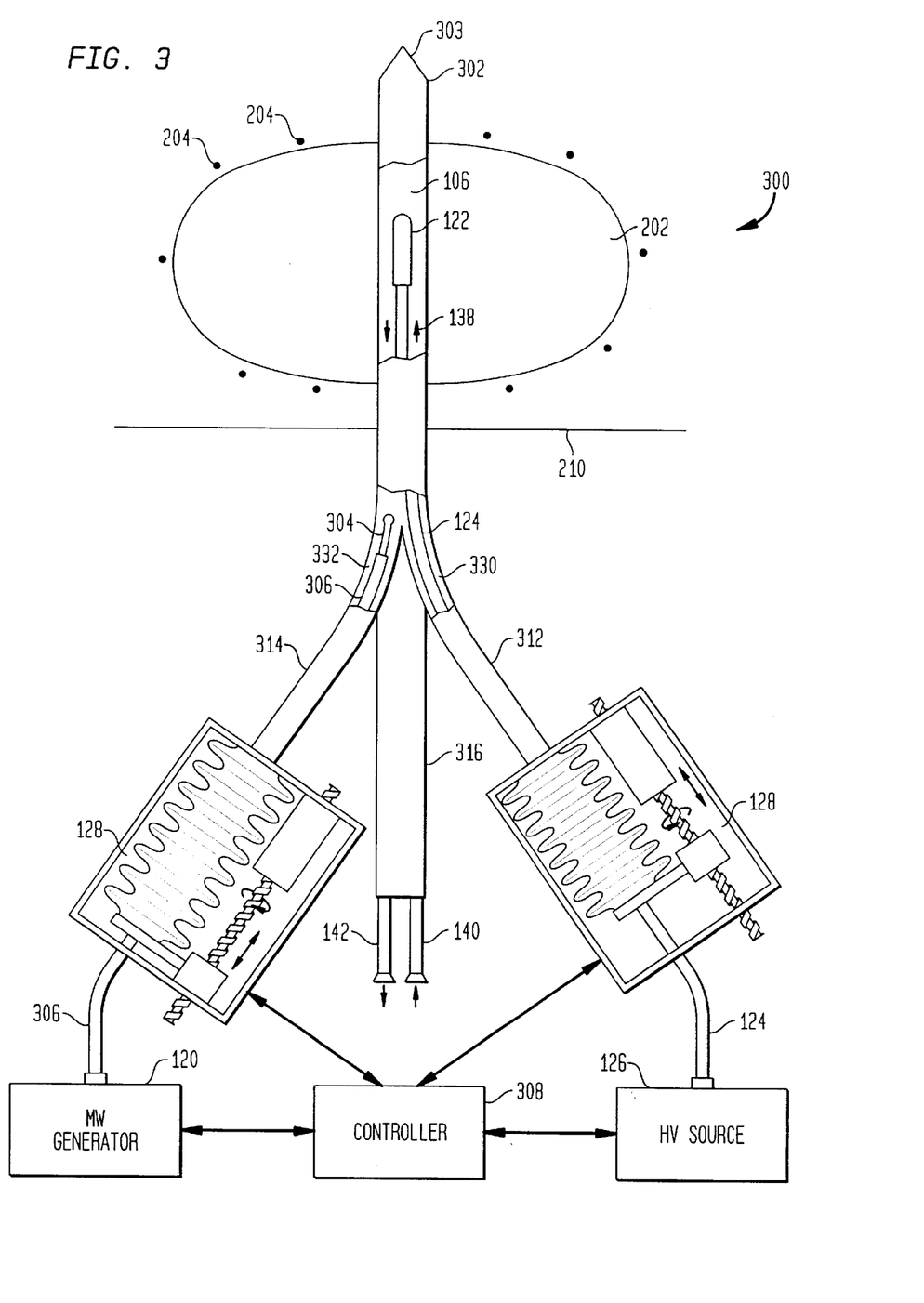
FIG. 3 is a schematic of a second embodiment of a device for treating a tumor or cancerous growth by alternating hyperthermia emission and X-ray radiation.

FIG. 3 shows a second embodiment of a device 300 for simultaneously treating a tumor or cancerous growth with hyperthermia and X-ray radiation. Device 300 has an introducer 302 comprised of a rigid plastic material, transparent to microwave radiation. Introducer 302 includes a sharp distal tip 303 for piercing skin 210 and for entering tumor 202. Device 300 is designed to allow alternative doses of microwave radiation and X-ray radiation. However, as would be apparent to one skilled in the relevant art, doses could be applied in any amount and at the same time.

FIG. 3 shows a cutout view of introducer 302. X-ray emitter 122 is located within hollow core 106 of introducer 302. Introducer 302 is connected to an X-ray leg 312 and a microwave leg 314, which each have a lumen 330 and 332. X-ray leg 312 and a microwave leg 314 are each connected to separate push-pull devices 128. High voltage miniature cable 124 extends from introducer 302 through lumen 330 of X-ray leg 312 and through push-pull device 128. As described above, X-ray emitter 122 is attached to high voltage miniature cable 124, which is connected to push-pull device 128. Also, as described above, push-pull device 128 can retract or advance high voltage miniature cable 124 and X-ray emitter 122. In this embodiment, push-pull device 128 can retract high voltage miniature cable 124 and X-ray emitter 122 to a point outside of the introducer 302 and into lumen 330 of X-ray leg 312.

Device 300 also includes a microwave antenna 304 connected to the distal end of a coaxial cable 306. Coaxial cable 306 extends through lumen 332 of microwave leg 314 and push-pull device 128. Thus, similar to high voltage miniature cable 124, coaxial cable 306 may be advanced and retracted by push-pull device 128. Microwave antenna 304 can be advanced into hollow core 106 of introducer 302, and retracted from hollow core 106 of introducer 302 into lumen 332 of microwave leg 314.

Coaxial cable 306 extends from microwave antenna 304 through push-pull device 128 to microwave generator 120. Similarly, high voltage miniature cable 124 extends from X-ray emitter 122 to high voltage source 126. Both microwave generator 120 and high voltage source 126 are electrically connected to a controller 308. Controller 308 is also electrically connected to push-pull devices 128. Controller 308 is a master controller coordinating sequential heating and irradiation of the tumor by advancing and retracting both X-ray emitter 122 and microwave antenna 304.

In use, controller 308 operates to activate high voltage source 126 when X-ray emitter 122 is properly positioned within introducer 302. Controller 308 also controls the movement of X-ray emitter 122 by means of push-pull device 128. As stated above, X-ray emitter 122 has a donut-like irradiation pattern.

Thus, in order to irradiate the whole tumor, X-ray emitter 122 is advanced or retracted while emitting X-ray radiation until all of tumor 202 has been properly treated. Controller 308 deactivates high voltage source 126 and activates push-pull device 128 to retract X-ray emitter to an idle position, in lumen 330 of X-ray leg 312. Controller 308 then activates push-pull device 128 to advance microwave antenna 304 from lumen 332 of microwave leg 314 into introducer 302. Once microwave antenna is properly positioned, controller 308 activates microwave generator 120 to provide hyperthermia treatment to tumor 202.

Temperature sensors 204 placed around the periphery of tumor 202 detect temperature of the tissue around tumor 202. Sensors 204 are coupled to leads (not shown) which, in turn, are coupled with a temperature reading unit (not shown). In one embodiment, the temperature reading unit is configured to electrically communicate with controller 308 to feedback information regarding the temperature of each sensor 204. Because of the mobility of microwave antenna 304 within introducer 302, controller 308 can be programed to advance or retract microwave antenna 304 to address hot or cool areas around tumor 202 by moving microwave antenna away from areas that are overly warm and towards areas that are cool, as would be apparent to one skilled in the relevant art.

Because of the heat generated from operation of microwave antenna 304 and X-ray emitter 122, cooling is provided to maintain introducer 302 at an acceptable temperature. In this embodiment, device 300 is provided with a cooling leg 316. Cooling leg 316 is fluidly connected to hollow core 106 of introducer 302. Cooling liquid is pumped into hollow core 106 through inlet 140. Fluid will flow through hollow core 106 and exit through outlet 142, as described above with reference to FIG. 1. Again, it is preferred that hollow core 106 be completely filled with the cooling fluid, as air pockets may affect the impedence and reflect energy, creating hot and cold spots in different regions of introducer 302.

In order to activate X-ray emitter 122, it is not necessary to completely withdraw microwave antenna 304 from introducer 302. It is only necessary to retract microwave antenna 304 to a position such that microwave antenna 304 and coaxial cable 306 do not interfere with the operation of and irradiation by X-ray emitter 122. Likewise, it is not necessary to completely withdraw X-ray emitter 122 from introducer 302 when performing microwave emission via microwave antenna 304. It is only necessary to retract X-ray emmitter 122 to a position such that X-ray emitter 122 and high voltage miniature cable 124 do not interfere with the treatment being performed by microwave antenna 304. Thus, X-ray emitter 122 and microwave antenna 304 may simultaneously occupy introducer 302.

Although X-ray leg 312, microwave leg 314 and cooling leg 316 are shown as distinct and separate components, two or all of these components could be combined into a single leg as would be apparent to one skilled in the relevant art.

Figure 4:
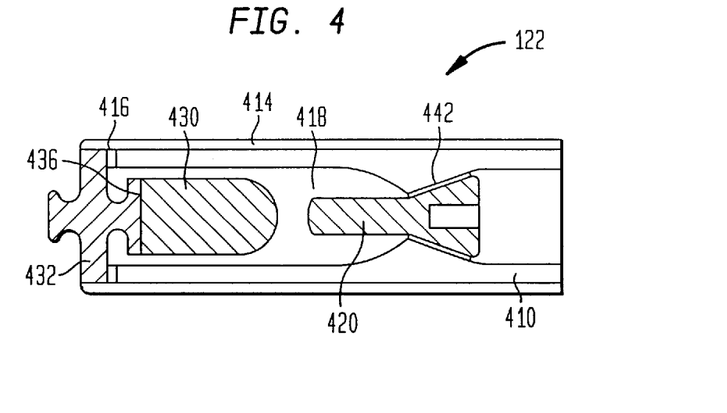
FIG. 4 is a miniature X-ray device for use in the embodiment of FIG. 1 or FIG. 3.

FIG. 4 shows a detailed view of X-ray emitter 122 of FIGS. 1, 2 and 3. X-ray emitter 122 comprises an insulating shell 410, an anode 420, a cathode 430 and a cathode cap 432. Insulating shell 410 can be comprised of any material having a very high dielectric strength (120–200 kV/mm) combined with high electrical resistivity ($10^{15}$ Ohm-cm), gas impermeability, and moderate mechanical strength. Insulating shell 410 should also have a coefficient of thermal expansion (CTE) close to that of anode 420. Finally, insulating shell 410 should have low to moderate absorption of X-ray within the energy range of 10–20 kV. Thus, the material should be composed of relatively low weight elements. Crystalline quartz and diamond both meet these requirements, and are good materials for the insulating shell. Platinum, tungsten or other heavy metals are good materials for the anode.

Insulating shell 410 is coated with a metal coating 414, which provides electrical contact between cathode cap 432 and the braid of a coaxial cable (not shown). Metal coating 414 may be any non-corrosive conductive metal, as would be known by one skilled in the relevant art, and is preferably silver.

Cathode cap 432 is brazed or bonded to cathode 430 at cathode bond 436, using any method known to one skilled in the relevant art, and provides an electrical contact between cathode cap 432 and cathode 430.

Cathode cap 432 has a cap brazing surface aligned to meet a shell brazing surface at braze 416. Insulating shell 410 includes a conical brazing surface brazed with a conical braze 442 to a conical anode brazing surface on anode 420. Anode 420 is electrically connected to an interior wire (not shown) of the coaxial cable, completing a circuit.

In use, cathode 430 is contained in an interior space 418 of insulating shell 410. Interior space 418 is kept as a vacuum environment. High voltage is applied through the braided portion of the coaxial cable to metal coating 414. The voltage is carried from metal coating 414 through the electrically connected cathode cap 432 to cathode 430. The applied voltage causes an electric field to generate around cathode 430, causing cathode 430 to emit electrons, which travel through the vacuum toward anode 420. As the electrons approach the anode, they are deflected by the positively charged nuclei of the anode material, losing energy and change band frequency into X-ray band.

One example of an X-ray emitter that is suitable for use in the present invention is disclosed in a co-pending application entitled, Miniature X-ray Device and Method of its Manufacture; U.S. Application No. 09/760,815, to Chornenkey et al.

Figure 5:
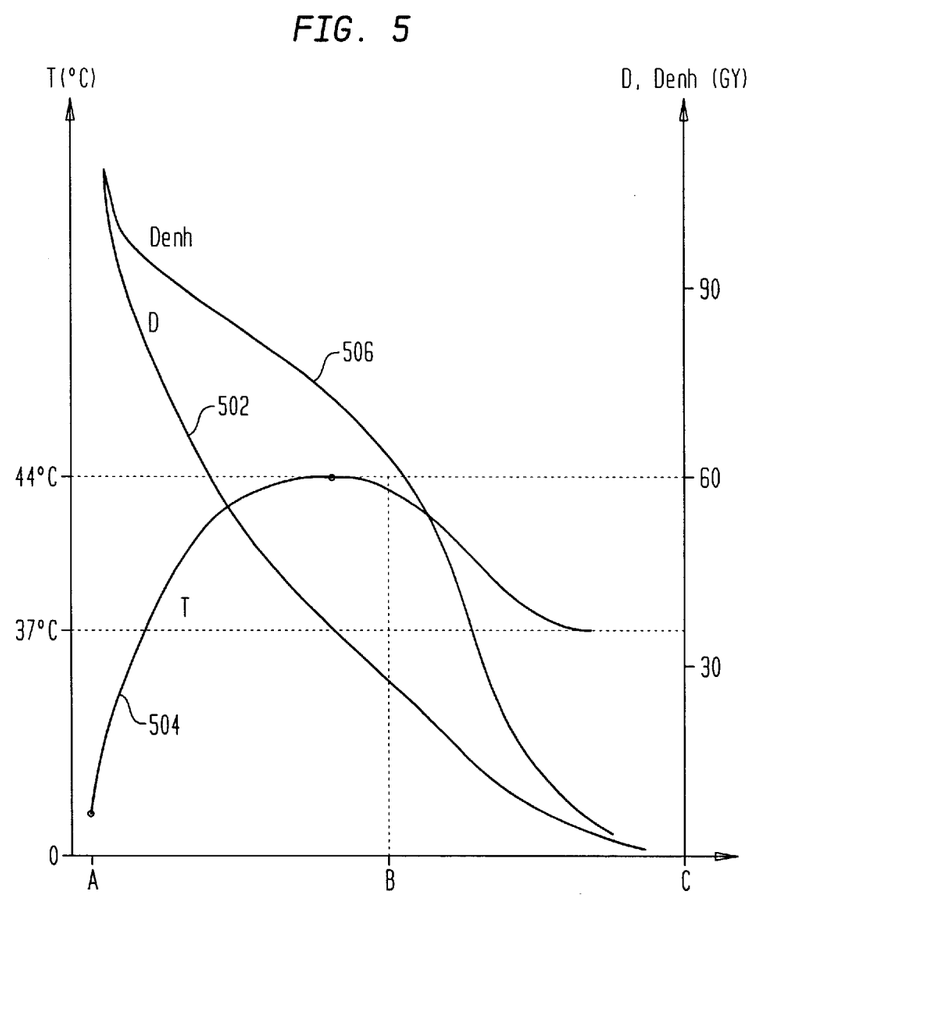
FIG. 5 is a graph showing curves of functions over a distance from the introducer axis.

FIG. 5 shows a qualitative plot of dose and temperature curves over a distance from the introducer axis. The horizontal axis of FIG. 5 is the distance from the introducer axis, with A being the introducer surface and B being boundary of the tumor. The function curves shown are Radiation Dose D marked as curve 502, Temperature Curve T marked as curve 504, and Radiation Dose Enhanced by Hyperthermia $D_{enh}$ marked as curve 506. The dose curve D, near the introducer is very high, near 100 Gy, which guarantees instant death of the irradiated cell even without any support from the hyperthermia. Curve D rolls off approximately at 1/(distance squared) to a value of about 25–30 Gy at the tumor's peripheral boundary. The radiation dose to be emitted is based on the size of the tumor to be treated, as would be apparent to one skilled in the relevant art.

Temperature curve T is controlled by the amount of microwaves emitted into the tumor and surrounding tissue. Near the introducer, temperature curve T is below the body level temperature of 37° C., as it is kept cool from direct contact with the introducer, which is liquid cooled as described above. Temperature curve T climbs to a maximum level of 43–44° C. from the middle to peripheral parts of the tumor and rolls off to almost body level temperature in healthy tissue beyond the tumor.

Radiation dose enhanced by hyperthermia curve $D_{enh}$, or enhanced dose curve, shows that hyperthermia enhances the killing power of ionizing radiation approximately two times. At the center of the tumor the introducer cools surrounding tissue, so that in spite of microwave heating the temperature is below body level. No enhancement of the killing power occurs near the introducer and the enhanced dose curve $D_{enh}$ closely follows the dose curve D. As seen by enhanced dose $D_{enh}$, the hyperthermia enhancement becomes significant near the middle and peripheral parts of the tumor, where it is needed most. As a result of the enhancement of the dose through applied heat, the cell-killing enhanced dose curve $D_{enh}$ is elevated inside the tumor and rolls off to low values over a short distance beyond the tumor. It should be noted that FIG. 5 is a qualitative curve. Application of heat does not, in reality, increase the dose of radiation, but actually lowers the cell's resistance to the dose of radiation, making the same dose nearly twice as powerful.

While the invention has been particularly shown and described with reference to preferred embodiments thereof, it will be understood by those skilled in the art that various changes in form and detail may be made therein without departing from the spirit and scope of the invention.

What is claimed is:

1. An apparatus for treatment of a tumor comprising:
   an introducer having a central axis and a hollow core;
   a miniature X-ray emitter capable of being disposed in said hollow core and movable along said central axis within said introducer;
   a microwave antenna for radiating microwave energy capable of being disposed in said hollow core and movable along said central axis within said introducer independent of said X-ray emitter; and
   means for cooling said introducer.

2. The apparatus of claim 1, wherein said microwave antenna and said miniature X-ray simultaneously occupy said introducer.

3. An apparatus for treatment of a tumor comprising:
   an introducer having a central axis and a hollow core;
   a miniature X-ray emitter capable of being disposed in said hollow core;
   a microwave antenna for radiating microwave energy capable of being disposed in said hollow core and movable within said introducer;
   means for cooling said introducer; and
   push-pull devices, wherein said microwave antenna and said X-ray emitter are connected to said push-pull devices such that said antenna and said X-ray emitter can be advanced or retracted in said introducer.

4. The apparatus of claim 1, wherein said cooling means is a liquid, said liquid being pumped into said hollow core of said introducer though an inlet and exiting said hollow core through an outlet.

5. An apparatus for treatment of a tumor comprising:
   an introducer having a central axis and a hollow core;
   a miniature X-ray emitter capable of being disposed in said hollow core;
   a microwave antenna for radiating microwave energy capable of being disposed in said hollow core and movable within said introducer;
   means for cooling said introducer; and
   a leg having a leg lumen, wherein said leg lumen is fluidly connected to said hollow core of said introducer, and wherein said X-ray emitter and said microwave antenna are capable of being advanced from said leg lumen into said hollow core of said introducer.

6. An apparatus for treatment of tumors, comprising:
   an introducer having a central axis and a hollow core;
   a miniature X-ray emitter capable of being disposed in said hollow core;
   means for radiating microwave energy, wherein said means for radiating microwave energy is a microwave antenna capable of being disposed in said hollow core;
   an X-ray leg having a lumen, said X-ray leg being coupled to said introducer, said X-ray emitter being disposed in said lumen of said X-ray leg and capable of being advanced from said lumen of said X-ray leg into said hollow core of said introducer;
   a microwave leg having a lumen, said microwave leg being coupled to said introducer, said microwave antenna being disposed in said lumen of said microwave leg and capable of being advanced from said lumen of said microwave leg into said hollow core of said introducer; and
   means for cooling said introducer.

7. The apparatus of claim 6, wherein said microwave antenna is movable along said central axis.

8. The apparatus of claim 6, wherein said X-ray emitter is movable along said central axis.

9. The apparatus of claim 6, further comprising:
   a push-pull mechanism for advancing and retracting said X-ray emitter within said introducer.

10. The apparatus of claim 6, wherein said X-ray emitter comprises a cathode, an anode and an insulating shell.

11. The apparatus of claim 6, wherein said introducer is in the shape of a needle.

12. The apparatus of claim 6, wherein said means for cooling is a fluid, wherein said fluid is pumped into said hollow core of said introducer through an inlet and exits said hollow core through an outlet.

13. The apparatus of claim 12, wherein said fluid is water or saline solution.

14. An apparatus for treatment of tumors comprising:
    a miniature X-ray emitter;
    a microwave generator coupled to an antenna;
    an introducer with a hollow core having a distal end adapted for placement into a tumor and a proximal end having first and second hollow legs communicating with said hollow core of said introducer, said first hollow leg being adapted for receiving said miniature X-ray emitter and said second hollow leg being adapted for receiving said microwave antenna, wherein said microwave antenna is movable inside said hollow core of said introducer from said second leg to said distal end of said introducer; and
    means for cooling said introducer.

15. The apparatus of claim 14, comprising a push-pull mechanism for advancing said microwave antenna within said introducer from said second leg to the distal end of said introducer.

16. A method of treating a tumor, comprising the steps of:
    (a) introducing an introducer to the proximity of the tumor, said introducer having a distal end and a hollow core, said hollow core communicating with first and second hollow legs connected proximally to said introducer, said introducer adapted for accepting into said distal end an X-ray catheter advanced from said first leg or a microwave antenna advanced from said second leg;
    (b) advancing said X-ray catheter into said introducer, irradiating the tumor, and retracting said x-ray catheter from said introducer;
    (c) advancing said microwave antenna into said introducer, emitting microwave energy into said tumor and retracting said microwave antenna from said introducer; and
    (d) cooling said introducer during steps (b) and (c).

17. The method of claim 16, further comprising the step of measuring the temperature about the periphery of the tumor prior to said step (c).

18. The method of claim 16, wherein said x-ray catheter is moved into a plurality of positions along said introducer for irradiating the tumor.

19. The method of claim 16, wherein said microwave antenna is moved into plurality of positions along said introducer for emitting microwave energy.

20. The apparatus of claim 14, wherein said X-ray emitter comprises a cathode, an anode and an insulating shell.

21. The apparatus of claim 14, wherein said means for cooling is a liquid, wherein said liquid is pumped into said hollow core of said introducer through an inlet and exits said hollow core through an outlet.

22. The apparatus of claim 21, wherein said liquid is water or saline solution.

* * * * *